United States Patent
Malnati Ramos et al.

(10) Patent No.: US 11,612,179 B2
(45) Date of Patent: Mar. 28, 2023

(54) METHOD FOR PRODUCING A NANOEMULSION WITH ENCAPSULATED NATURAL ANTIOXIDANTS FOR PRESERVING FRESH AND MINIMALLY PROCESSED FOODS, AND THE NANOEMULSION THUS PRODUCED

(71) Applicant: Miguel Enrique Jesus Malnati Ramos, Lima (PE)

(72) Inventors: Miguel Enrique Jesus Malnati Ramos, Lima (PE); Melissa Ximena Adriazola Du-Pont, Lima (PE); Daniel Ali Oviedo Morales, Lima (PE)

( * ) Notice: Subject to any disclaimer, the term of this patent is extended or adjusted under 35 U.S.C. 154(b) by 151 days.

(21) Appl. No.: 16/641,426

(22) PCT Filed: Aug. 23, 2017

(86) PCT No.: PCT/PE2017/000014
§ 371 (c)(1),
(2) Date: May 6, 2020

(87) PCT Pub. No.: WO2019/039947
PCT Pub. Date: Feb. 28, 2019

(65) Prior Publication Data
US 2020/0329743 A1    Oct. 22, 2020

(51) Int. Cl.
*A23L 3/3472*    (2006.01)
*A23P 10/30*    (2016.01)
*A23B 7/16*    (2006.01)

(52) U.S. Cl.
CPC ............ *A23L 3/3472* (2013.01); *A23B 7/16* (2013.01); *A23P 10/30* (2016.08)

(58) Field of Classification Search
CPC ........... A23L 3/3472; A23P 10/30; A23B 7/16

USPC ............................................... 426/543
See application file for complete search history.

(56) References Cited

U.S. PATENT DOCUMENTS 2,577,232 A * 12/1951 Cole .................. C08B 37/0045
                                                     536/2
2014/0205722 A1 * 7/2014 Quintanar Guerrero ...................
                                                     A23L 3/3463
                                                     426/310

FOREIGN PATENT DOCUMENTS

EP          2698066 A2 * 2/2014 ............. A23B 7/154

OTHER PUBLICATIONS

Kosegarten & Jiménez et al (2012); Factores principales que intervienen en la estabilidad de una emulsión doble; Temas Selectos de ingenieria de Alimentos.
(Continued)

*Primary Examiner* — Brent T O'Hern
(74) *Attorney, Agent, or Firm* — Eugenio J. Torres-Oyola; Rafael Rodriguez-Muriel; Victor M. Rodriguez-Reyes

(57) ABSTRACT

A process for producing a nanoemulsion formulation comprising the following main stages: (a) extraction of natural antioxidants from peels or seeds of fruits, vegetables or cereals, wherein the extraction is carried out with pure water, with a concentration of the extracted natural antioxidants with a vacuum distillation method between 0.5-15 inHg at 20-60° C. for 10-95 minutes until the concentration of the extracted natural antioxidants is between 10-50 wt % and then a tangential nanofiltration of the concentrated natural antioxidants; (b) encapsulation of the natural antioxidants; (c) formation of a nanoemulsion; and (d) cryodrying of the formed nanoemulsion.

10 Claims, 1 Drawing Sheet

(56) References Cited

OTHER PUBLICATIONS

Llabot et al. (2008); Nanopartículas poliméricas sólidas; Research Gate.
Miguel A. Meneses et al (2015); Antioxidant phenolic compounds recovery from *Mangifera indica* L. by-products by supercritical antisolvent extraction; Journal of Food Engineering.
Enrique Morales-Avila et al (2016); Preparation and Evaluation of a Food Additive Based on Polymeric Nanoparticles for Controlled Delivery of Antioxidant Extracts; Current Nutrition & Food Science; cited at IPER PCT.

* cited by examiner

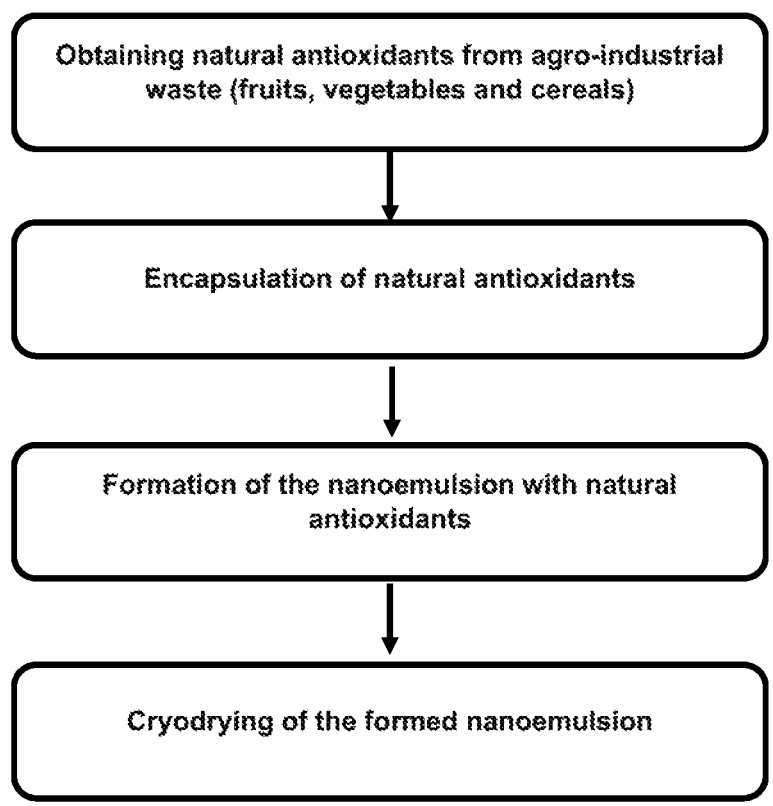

METHOD FOR PRODUCING A NANOEMULSION WITH ENCAPSULATED NATURAL ANTIOXIDANTS FOR PRESERVING FRESH AND MINIMALLY PROCESSED FOODS, AND THE NANOEMULSION THUS PRODUCED

TECHNICAL FIELD

The present invention refers to methods for optimal extraction and encapsulation within a nanoemulsified matrix, applicable particularly to the preservation of fresh fruit, vegetables, cereals, juices and minimally processed food for humans or animals; it also comprises the optimized formulation and encapsulation.

This invention is comprised in the technical field of nanotechnology and food industries, bioindustry, biotechnology and agribusiness derivatives.

STATE OF THE ART

Edible films are dispersed emulsions made up by the homogenization of immiscible substances which may be categorized in three different types, a) oil: water (O/W), b) water: oil (W/O), c) multi-emulsion (W/O/W or O/W/O), each of which depends on the element to be dispersed on the majority matrix. These are commonly used to preserve the shelf life of foods, through polysaccharides with microbial power such as chitosan, which preserves the shelf life of post-harvest fruits and vegetables, or other foods such as eggs, legumes or even cereals, by increasing the antimicrobial capacity of these fresh products.

Currently, research, development and innovation of edible films in the field of preservation of foods such as fruits and vegetables are increasingly developed due to climate change that affects all countries in the world and the imminent deterioration of food in general due to exposure to environmental conditions. In addition, the desire of logistics and agro-industrial companies to preserve with methods that use less and less energy, compared to current techniques such as freezing and preservation with controlled atmosphere, encourages this type of products. Fortunately, technology evolved and edible films were developed at a smaller particle size, at a micrometric scale, which allowed for better application on the food surface and greater thermodynamic stability over time, compared to normal droplet size emulsions. However, the use of chemical surfactants to achieve the spontaneous formation of these microemulsions became a problem, as the products became toxic. For this reason, the nanotechnology of emulsions was effectively developed, which provided them with kinetic stability, thanks to homogenization processes at high speeds and pressures, with which the use of surfactants was reduced to a minimum.

Thus, nanoemulsions are stable compositions, molecularly composed mainly of a water-oil mixture, so the internal particles are in a nanometric range between 20-500 nm. These nanometric mixtures are characterized and considered the best means to facilitate the transport, release and absorption of functional active agents such as antioxidants, antimicrobials or even nutraceuticals (Cardoso & Jimenez, 2015); they also exhibit low sensory perception and therefore have various uses in sectors such as pharmaceuticals, cosmetics, medicine or even food. However, the global trend was the use of natural or organic products that are free of inputs harmful to health, or a superfoods-related approach, which influenced the development of products with active agents extracted from natural compounds, so the trend enriched edible films for foods with essential oils from aromatic vegetables such as oregano, rosemary, cinnamon and other antioxidants, which contain phenolic compounds that give these additional characteristics useful for the preservation of foods with additional nutritional properties, required by the market.

The functional active agents extracted in industrial processes may be polyphenols, terpenes, glycosides or alkaloids, depending on the raw material used. For example, polyphenols are abundant in fruits, in the form of phenolic compounds while terpenes are found in the essential oil of aromatic herbs. Flavonoids are phenolic compounds characterized in that they represent a major source of antioxidants that help reduce the oxidative stress of lipids, proteins and nucleic acids due to the surrounding oxygen in the environment (Cerón, Higuita & Cardona, 2010). However, scientific advances in food biotechnology contributed to the reuse of various active agents, such as flavonoids, present in waste with high antioxidant potential, found in the peels and seeds of various fruits. Therefore, countries with great biodiversity, such as Peru, must take advantage of the agro-industrial waste to transform it and produce additives based on antioxidants that can make various food products functional, i.e. nourish and prevent diseases, so that it is commercially viable and environmentally sustainable. In addition, natural phenolic compounds are increasingly accepted by industries and world institutions, such as the FAO (Food and Agriculture Organization of the United Nations), which demands safe food, free from bacterial contamination and toxicity caused by synthetic additives commonly used in the food industry (Conte et al, 2007); however, phenolic compounds have the technical problem of volatility and sensitivity due to their chemical composition, which represented a problem to effectively preserve them, in addition to the use of inorganic chemical inputs for the extraction and concentration stages damaging the edible condition of the product. In this way, technologies such as compound nanofiltration and encapsulation were developed to preserve the active compounds, at different particle sizes of volatile compounds, such as antioxidants or other products such as omegas, vitamins, proteins and others, which contribute to maintaining and/or improving the nutritional and organoleptic characteristics over time, of minimally processed foods.

In the state of the art there are invention patents related to the production of nanoemulsions for the preservation of food in general, which use extensive and inaccurate homogenization processes at high speeds and pressures, or by mechanical fragmentation with the use of chemical surfactants, with which water-oil emulsions of fine granulometry below 100 nanometers (nm) are obtained; also patent applications such as EP728460 or EP1016453 use chemical surfactants or polyols to stabilize the emulsion and obtain the desired granulometry. Patent US20140205722A1 mentions the composition of a complex solid lipid nanoparticle that preserves fruits, vegetables, seeds and/or cereals for long periods of time based on a lipid base made up of waxes, and additional inputs such as proteins, antioxidant agents and film-forming materials. There are also patents such as KR20140115427 and KR20160005182A that propose nanoemulsions that do not mention the efficient extraction processes of their active compounds, and present inaccurate processes for curcumin and cinnamon oil antioxidant solutions due to their antimicrobial functional principle; these are obtained through a mixture between the emulsifier and water, followed by an oil and antimicrobial agent mixture, to finally mix both products by high pressure. Finally, patent CN104997129 proposes extensive processes of a food additive using vegetable compounds, for which the input with the active compound (Larix tree) is pulverized and extracted by ultrasound using ethanol as a chemical solvent at 60-70° C. for 30-50 minutes, then it is concentrated with chemical additives such as sulfuric acid to finally centrifuge and crystallize.

Regarding the extraction of antioxidant compounds, methods with organic solvents or hydrothermal treatments with recirculation are used. Patent WO2004009206A1 is a process for the extraction of phenolic compounds that uses reactors at temperatures between 180°-240° C. for up to 30 minutes in reaction and then allows it to cool for hours and remove the filtered liquid fraction, which does not preserve the antioxidant characteristics given the temperatures used and is not efficient. Patent ES2198286T3 is a new process for producing natural antioxidants that consists in extracting with organic solvents at temperatures up to 100° C. with rapid cooling, evaporation of the organic solvent, distillation of the solution and drying in a fluidized bed; this means too many extensive processes and the use of chemicals to obtain the final product.

Patent US2016262438 mentions a method for the extraction of phenols, which is based on the concentration of antioxidant juice up to a Brix degree of 25°, then it is subjected to adsorption processes with resins and ethanol as solvent, finally it is concentrated in a rotovap to be sprayed with the Spray Dryer method; this demands extensive, complex and high cost processes for the lengthy processes. Finally, patent CN104305468 is an extensive method that uses chemicals for the preparation of sesame antioxidant, which consists in drying the seeds, performing a "degreasing" process with n-hexane and an extraction with ethanol in high concentration for a period of 1 day, to finally be concentrated in a rotovap. The use of nanofiltration technology for the concentration and purification of antioxidant solutions has not been registered in the state of the art. Patent ES2294696T3 shows a method that includes several nanofiltration stages of albumin solutions until the desired purity and concentration is achieved.

Regarding the active compounds encapsulation techniques, these are used in very diverse fields, from pharmaceuticals to agrochemicals. The techniques employed include the use of polymeric materials to wrap the active agents involved, followed by techniques to produce capsules in particle size, increasingly smaller, resulting from spray drying or supercritical fluid processes or, in exceptional cases, cryodrying processes with solvents. Patent ES2213572T3 is a complex but industrially viable process for microencapsulating water-soluble substances, which involves a mixture of the substance with biodegradable polymers and a chemical solvent to homogenize the sample under ideal conditions for the formation of the microparticle, which solidifies through the removal of this solvent. Patent ES2268073T3 is a process for microencapsulating agricultural active agents, for which they mix chemical materials with a high melting point and another with a normal melting point, which are heated until they become liquid and through interfacial polymerization processes they become a solid state microcapsule; this means that the microencapsulated antioxidant can deteriorate due to an excessive exposure to heat.

On the other hand, the following non-patent document has been identified, which we also cite as background: Memorias del XXXIV Encuentro Nacional and III Congreso Internacional de la AMIDIQ (Proceedings of the XXXIV National Meeting and III International AMIDIQ Congress). Mazatlan, Sinaloa, Mexico. May 7-10, 2013. M. G. Michel Barba, et al. Efecto de los parámetros de procesamiento de la microfluidización sobre las propiedades fisicoquímicas de nanoemulsiones (goma arábica-aceite de linaza) (Effect of microfluidization processing parameters on the physicochemical properties of nanoemulsions (gum arabic-linseed oil) pags.: 2738-2743. ISBN: 978-607-95593-1-1. This publication describes a method for making a microemulsion from linseed oil and gum arabic. A colloidal dispersion is formed from dissolved and filtered gum arabic. The emulsion sample is prepared with 3% w/w dispersed phase in relation to gum arabic: linseed oil equal to 2:1. Thus, a thick emulsion is formed where the linseed oil is added drop by drop to the colloidal dispersion of the gum arabic, using a high cut disperser, at 5000 RPM for 10 minutes at a temperature of 20° C. This thick emulsion was then homogenized in a microfluidizer, in triplicate. Deionized water was used for all the work. However, this process differs in terms of the temperature, time and rpm parameters used during the process.

Therefore, it is necessary to have a process to produce nanoemulsions with high antioxidant power from fruit and/or vegetable and/or cereal waste, efficiently encapsulated, and easily processed without organic chemical additives in the final product, which contribute to preserving and/or improving the nutritional and organoleptic characteristics in fresh and minimally processed foods, for humans and animals, with food grade.

BRIEF DESCRIPTION OF THE INVENTION

There is a growing need for products that contribute to the preservation of food and other natural products, which do not include elements, substances, synthetic or artificial derivatives and which in turn have nutraceutical properties, are easy to produce and environmentally friendly, reducing the environmental impact of the industry that uses vegetable inputs such as fruits, vegetables and cereals and discards organic material waste.

The present patent application proposes a solution to the problem described.

The invention comprises a method for producing a preservative suspension, hereinafter referred to as nanoemulsion, which contains active agents encapsulated at a nanometric scale; the formulation of such product and its application for the preservation of different products or natural food derivatives such as fresh or minimally processed fruits, vegetables and cereals and juices are disclosed.

In that sense, the object of the invention is the development of a method to produce nanoemulsions with high antioxidant power from fruit and/or vegetable and/or cereal waste, efficiently encapsulated, and easily processed without organic or food grade chemical additives in the final product, which contribute to preserving and/or improving the nutritional and organoleptic characteristics in fresh or minimally processed products, for humans and animals, with food and nutraceutical grade.

The core aspect of the invention consists of a thin nanometric layer on the food that prevents the exchange of gases and fluids with the environment, enhanced with selected antioxidants whose function is similar to an enzyme that delays or inhibits the biochemical reactions of food decomposition and oxidation. This allows fresh and minimally processed foods to have a longer shelf life and foods intended for freezing to improve their organoleptic quality when thawed.

DETAILED DESCRIPTION OF THE INVENTION

The present invention was developed as a solution to the above mentioned technical problem. It proposes a novel formulation of a dispersed system as a nanoemulsion enhanced with natural edible antioxidants extracted from fruit and/or vegetable and/or cereal waste, the encapsulation and cryodrying processes of the nanoemulsion, and this finished product that ensures stability, prolonged and effective action over time on fresh and minimally processed foods that have been protected with this product, such as fruits, vegetables and cereals.

The object of the invention is the process for producing a nanoemulsion with natural antioxidants, which comprises the following stages a) the efficient production of the natural antioxidants, b) the encapsulation of the natural antioxidants, c) the formation of the nanoemulsion with natural antioxidants, and d) the cryodrying of the formed nanoemulsion.

The efficient production of natural antioxidants from fruit, vegetable and cereal waste includes the following processes:

Sorting, washing and disinfecting the peels and seeds of selected fruit, vegetable or cereal waste.

Dehydration of the disinfected raw material, which can be done in a conventional oven at 30-60° C. for about 2-6 hours with hot air in reflux, or by freeze-drying at temperatures between −30 to −50° C. and an absolute vacuum pressure of at least 0.04 mbar, for 10-15 hours, depending on the sensitivity of the antioxidant component of the fruit, vegetable or cereal.

Extraction with polar solvents such as ultra-pure water, of the dehydrated waste with active potential produced in the previous stage, with a humidity degree of between 2-20%, which can be done by microwave-assisted extraction at a power between 100-400 W for 5-40 minutes, or ultrasound with a vibration power between 20-60 kHz, for 10-40 minutes, at a temperature between 30-60° C., depending on the sensitivity of the antioxidant component of the fruit, vegetable or cereal.

Partial concentration of the antioxidant extract with the simple distillation method in a rotovap under vacuum between 0.5-15 inHg at 20-60° C. for 10-95 minutes until a concentration between 10-50% is achieved.

Tangential nanofiltration of the concentrated antioxidant solution at a pH between 6-10.5, in two sequential filters with nanopores between 10-100 nm and minimum surface area of 0.01 m$^2$, at the same temperature as the previous process, through which the pumped solution passes at pressures between 0.5-1 bar.

The encapsulation of the natural antioxidants comprises the following processes:

Mixing at a speed between 500-2000 RPM, at a temperature between 20-60° C. for 1-3 hours of the concentrated antioxidant extracts in a 1:1 mixture with polysaccharides such as maltodextrin and gum arabic, or a direct proportion of modified starch from corn or cassava, in an amount that replaces the percentage of soluble solids measured with refractometry techniques, of the selected antioxidant solution.

Homogenization at a speed between 8000-15000 RPM for about 1-15 minutes to encapsulate the active compounds with the biopolymers and thus protect them from damage by subjection to the environment, based on the formation of a microemulsion with a wall material that will provide such protection. The resulting antioxidant microemulsion is stored temporarily under refrigeration at a temperature of 5-15° C.

The formation of the nanoemulsion with natural antioxidants comprises the following steps:

Dilution of alginic acid in drinking water, at a temperature of 50-70° C., with constant movement for 1-3 hours at 500-1500 RPM.

Homogenization at a speed of 8000-15000 RPM for about 1-15 minutes of the alginic acid in solution with the rest of the components: oily matrix, polysorbate, glycerol and the antioxidant microemulsion.

Microfluidization at high pressures of 100-200 MPa for 3-5 cycles, which produced the fluid nanoemulsion, enhanced with natural antioxidants from fruit and/or vegetable and/or cereal waste.

Finally, the cryodrying of the nanoemulsion produced in the previous stage includes the concentration of the nanoemulsion by means of cryodrying methods such as the freeze-drying process subjected to vacuum pressures of at least 0.04 mbar and temperatures between −10 and −50° C., which give it a powdery appearance, of reduced volume.

An advantage of the present invention is that the concentration is reduced to less than 2 hours and without using inorganic chemical solvents, in order to increase the naturalness of the product, the food grade and the efficiency of the process by 20-40%.

Another advantage of the invention is that it is not made up of proteins of any kind and the oily matrix used is a combination of saturated and monounsaturated fatty acids that present molecular stability due to the reduced number of double bonds in their molecules, such as coconut, canola, almond, avocado or peanut oil that provide the desired permeability and oxidative stability to the nanoemulsion, in addition to oleic acid that provides a functional characteristic to the final product.

Another advantage of the invention is that the refractometry method used in the encapsulation contributes to decreasing the freeze-drying time by 20-30%.

Another advantage of the invention is that the final product that is a concentrated nanoemulsion in powder, which decreases its volume by more than 100% with respect to the fluid nanoemulsion, contributes to improving the logistic processes of the product, and the product—when rehydrated—will maintain all its properties and particle size. Finally, an advantage of the product applied on minimally processed foods such as fruits, vegetables and cereals is that the storage conditions will be superior, avoiding long freezing chains and controlled atmosphere, since the cover of the colloidal suspension will allow preserving the food under refrigeration conditions, given the permeable principle and its enrichment with active agents of the fruit, vegetable or cereal waste.

One objective of the invention is to produce antioxidants with high phenolic concentration, from the waste of various fruits, vegetables or cereals, characterized by a formula rich in active antioxidant functional compounds.

Another objective of the invention is to produce a composition consisting of:

a) 0.5-10% alginic acid, preferably sodium or potassium alginate from natural sources, food grade (b) 0.1-10% oily matrix with saturated and/or monounsaturated fatty acids as main compounds (c) 0.1-1% polysorbates, preferably polyoxyethylene sorbitan monolaurate or polyoxyethylene sorbitan monostearate, food grade (d) 0.5-10% glycerol, preferably glycerol esters of rosin from natural plant sources, food grade e) 0.2-40% antioxidant microemulsion An alternative to the invention is a formulation intended to maintain the shelf life of cut fruits under refrigeration conditions. The solution is composed of the formulation presented, replacing glycerol and polysorbate with an amount of 1-5% calcium ascorbate or a 1:1 combination of ascorbic acid and citric acid.

Another alternative to the invention involves a microemulsified matrix, no longer at the nanometric scale, containing correctly encapsulated antioxidants, and presenting the same field of action for food preservation, since it involves all the process described, except for the microfluidization process, which is responsible for bringing the emulsion to a nanometric scale.

Another alternative of the invention, for use as an input in organic agriculture, consists of a formulation that lacks polysorbate since, according to the Equivalence Programs of different regulatory entities in the world, the chemical parameters evaluated are primarily traces of quaternary ammonium according to ISO 17025.

Another alternative of the invention, for use as an input to preserve the quality of natural fruit juices, also excludes the use of polysorbates in its formulation, since it generates an undesirable increase of the viscosity of the final product up to 50%.

The invention represents an improvement in the state of the art, since it proposes a simple method with a unique composition that improves production efficiency, with a higher antioxidant and functional percentage of the nanoemulsion, in addition to maintaining the naturalness and food grade, through techniques that do not use organic chemical additives such as ethanol, methanol or hexane, nor temperatures above 60° C. for the processes of extraction, concentration and encapsulation, which helps to maintain intact the polyphenols present in natural antioxidants extracted from fruit, vegetable and cereal waste.

The invention also implies an effective method for efficiently encapsulating active compounds such as proteins, fatty acids, vitamins and minerals, which have been correctly extracted from fruits, vegetables or cereals and are to be preserved over time, by means of emulsions that efficiently encapsulate the active agent.

BRIEF FIGURE DESCRIPTION

FIG. 1. Flow chart of the process of the invention detailing its four main stages.

EXAMPLE OF PREFERRED EMBODIMENT OF THE INVENTION

A. Process for Producing the Nanoemulsion with Encapsulated Natural Antioxidants A preparation of the nanoemulsion of the invention, by way of example, involves the selection, washing and disinfection of the peels and seeds of the mango fruit *Mangifera indica* L. with 100 ppm of sodium hypochlorite diluted in ozonized water; it is then dried with a tray freeze-dryer at a temperature of approximately −40° C. and an absolute vacuum pressure of at least 0.04 mbar, for 12 hours. Once the dehydration is completed, the degree of humidity of the raw material is measured and it is extracted with polar solvents by microwave assisted extraction at a power of 200 W for 20 minutes; the antioxidant extract is then partially concentrated using the simple distillation method in a rotovap under vacuum at 0.5-15 inHg at 40° C. for 60 minutes until a concentration of at least 15% is achieved, to pass through the tangential nanofiltration of the concentrated antioxidant solution in two sequential filters with 50 nm nanopores and minimum surface area of 0.01 m$^2$, at the same temperature as the previous process, through which the pumped solution passes at pressures between 0.5 bar. In a separate process, the concentrated antioxidant extracts are mixed at a speed of 500 RPM, at 25° C. for 2 hours in a mixture in direct proportion to the percentage of Brix degrees of the modified corn starch concentrate; it is homogenized in an industrial mixer at a speed of 12,000 RPM for about 5 minutes to encapsulate the active compounds, the resulting antioxidant microemulsion is stored temporarily under refrigeration at a temperature of 5-15° C. The alginic acid is diluted in ozonized water at 50° C., with constant movement for 1 hour, and then it is homogenized with the rest of the inputs: oily matrix, polysorbate, glycerol and the antioxidant microemulsion. Then followed the microfluidization process at high pressures of 100 MPa for 3 cycles, which produced the fluid nanoemulsion, enhanced with natural antioxidants from fruit and/or vegetable waste. Finally, the nanoemulsion produced in the previous stage was cryodried at vacuum pressures of at least 0.04 mbar and temperatures of −40° C., which gives it a fine granulometry solid appearance.

B. Application of the Nanoemulsion with Encapsulated Natural Antioxidants on Selected Foods The fruits and vegetables subjected to the experiment (mango, avocado, mandarin, strawberry and asparagus) were selected considering optimal quality characteristics, i.e. uniform sizes, shapes, colors and absence of post-harvest mechanical or phytosanitary damage, half-ripe, washed and disinfected with 100 ppm of sodium hypochlorite; then, the fluid nanoemulsion was applied in the form of a spray for 5 minutes and dried—drained for another 5 minutes—, at room temperature of 25±2° C. on harmless grids; then the food was packed in containers recommended by CODEX Alimentarium. Once the application protocol of the nanoemulsion of the invention was completed, accelerated controlled tests were carried out in triplicate, every 7 and 14 days under a temperature of 25±2° C. and relative humidity of 80-90%, with the exception of the strawberry and asparagus, which were refrigerated at 10±2° C., all the tests at the same product concentration. The samples were experimental lots of 1 kg of *Mangifera indica* L. mango, *Persea americana* avocado, *Citrus reticulata* mandarin, *Fragaria vesca* L. strawberry and *Asparagus officinalis* asparagus. The variables measured were weight differential, Brix degrees differential and hedonic scale, based on a Sensory Evaluation test. The evaluation was performed on a scale from 1 to 5, being 5 the scale of better acceptance according to the taste of the product, before a panel of 15 previously trained tasters. The results evidence that the experimental samples filmed with the invention show a remarkable improvement compared to the control samples without any treatment, since these—after 8-12 days—, depending on the fruit, were in a state of putrefaction. It should be noted that the tests were conducted at extreme temperatures, so that the samples at refrigeration temperatures between 5-10° C. increase their quality by at least 50%, which is beneficial for the agro-industrial sector, which manages even freezing temperatures and even controlled atmospheres to maintain the quality of the food product.

| Day Zero | | | |
|---|---|---|---|
| Sample | °Brix | Taste | Δ pH |
| Mango | 10.0 ± 0.05 | 5.0 ± 0.35 | |
| Avocado | 8.8 ± 0.05 | 5.0 ± 0.15 | 6.0 ± 0.05 |
| Mandarin | 10.8 ± 0.04 | 4.3 ± 0.40 | 3.15 ± 0.05 |
| Strawberry | 9.1 ± 0.05 | 5.0 ± 0.10 | 3.8 ± 0.03 |
| Asparagus | | 5.0 ± 0.40 | 5.0 ± 0.03 |

| Day 7 | | | | |
|---|---|---|---|---|
| Sample | ΔWeight | Δ°Brix | Taste | Δ pH |
| Mango | 0.04 ± 0.05 | 0.38 ± 0.05 | 4.5 ± 0.30 | |
| Avocado | 0.12 ± 0.05 | 0.50 ± 0.03 | 4.4 ± 0.35 | 0.05 ± 0.02 |
| Mandarin | 0.10 ± 0.04 | 0.45 ± 0.05 | 4.0 ± 0.25 | 0.05 ± 0.01 |
| Strawberry | 0.12 ± 0.05 | 0.35 ± 0.04 | 4.4 ± 0.30 | 0.05 ± 0.02 |
| Asparagus | 0.10 ± 0.05 | | 4.4 ± 0.30 | 0.15 ± 0.01 |

| Day 14 | | | | |
|---|---|---|---|---|
| Sample | ΔWeight | Δ°Brix | Taste | Δ pH |
| Mango | 0.24 ± 0.04 | 0.82 ± 0.05 | 3.9 ± 0.20 | |
| Avocado | 0.39 ± 0.05 | 1.10 ± 0.05 | 3.7 ± 0.30 | 0.35 ± 0.02 |
| Mandarin | 0.33 ± 0.05 | 0.85 ± 0.04 | 3.8 ± 0.25 | 0.30 ± 0.02 |
| Strawberry | 0.35 ± 0.05 | 0.85 ± 0.05 | 3.9 ± 0.25 | 0.25 ± 0.01 |
| Asparagus | 0.30 ± 0.05 | | 3.8 ± 0.35 | 0.30 ± 0.01 |

| Day 14 | | | |
|---|---|---|---|
| CONTROL SAMPLE | °Brix | Taste | Δ pH |
| Mango | 20.2 ± 0.04 | 0 ± 0.0 | |
| Avocado | NC | 0 ± 0.0 | NC |
| Mandarin | 15.6 ± 0.05 | 0.8 ± 0.25 | NC |
| Strawberry | NC | 0 ± 0.0 | NC |
| Asparagus | | 0 ± 0.0 | NC |

The biochemical degradation of food, caused largely by oxidative processes, is the main non-microbial factor where the free radicals formed initiate spoilage reactions that act mainly on lipids and proteins (Descalzo, Rizzo, Rossetti, Negri, Paéz, Costabel and Taverna, 2010), which can be counteracted with the invention containing properly encapsulated antioxidants.

Therefore, the experimental results obtained for asparagus can be extrapolated to cereals, since asparagus, a representative of vegetables, has similar proportions of essential amino acids, which reflects the protein similarity between both classes of foods.

TABLE

| Amino Acid Content in Representative Cereals and Asparagus | | | | |
|---|---|---|---|---|
| Essential Amino Acids | Quinoa (g/100 g protein)[3] | Kiwicha (g/100 g protein)[3] | Corn (g/100 g protein)[1] | Asparagus (g/100 g protein)[2] |
| Isoleucine | 6.9 | 5.2 | 4.0 | 6.9 |
| Leucine | 6.7 | 4.6 | 12.5 | 8.3 |
| Lysine | 6.8 | 6.7 | 2.9 | 8.9 |
| Methionine | 3.3 | 3.5 | 4.0 | 2.7 |
| Phenylalanine | 6.9 | 3.5 | 8.6 | 6.0 |
| Threonine | 4.5 | 5.1 | 3.8 | 5.7 |
| Tryptophan | 1.3 | 1.1 | 0.7 | 2.3 |
| Valina | 4.5 | 4.5 | 5.0 | 9.1 |

[1]Source: FAO (2013), Dietary protein quality evaluation in human nutrition
[2]Source: Alimentos.org.es (s/n), Aminoácidos de los Espárragos
[3]Source: Ayala, G. (2014), Aporte de los cultivos andinos a la nutrición humana On the other hand, samples of minimally processed foods and juices were evaluated, in experimental lots in triplicate, of 500 g of peeled and cut *Malus communis* apples and 500 ml of *Musa paradisiaca* banana juice with a minimum of 15-20% fruit, under controlled conditions of 20±2° C. and 70% relative humidity. The measurement was performed using the hedonic scale, based on a Sensory Evaluation test, with a scale from 1 to 5, being 5 the scale of best acceptance. The sensory criteria were taste, smell and sight, before a panel of 15 previously trained tasters, and pH to analyze the degree of acidity taken by the fruit. The experimental samples show a considerable improvement over the untreated control samples and the pH ranges remain within the fruit standard.

| Day Zero | | | | |
|---|---|---|---|---|
| Sample | Taste | Sight | Smell | pH |
| Apple | 4.5 ± 0.5 | White Color | 5.0 ± 0.5 | 4.5 ± 0.05 |
| Banana Juice | 5.0 ± 0.5 | Light Yellow Color | 5.0 ± 0.1 | 5.0 ± 0.04 |

| Day 5 | | | | |
|---|---|---|---|---|
| Sample | Taste | Sight | Smell | pH |
| Apple | 3.4 ± 0.4 | White Color with Light Brown Borders | 3.7 ± 0.4 | 4.1 ± 0.05 |
| Banana Juice | 3.1 ± 0.3 | Slightly Light Yellow Color | 3.5 ± 0.5 | 4.7 ± 0.05 |

| CONTROL SAMPLE | Day 5 | | | |
|---|---|---|---|---|
| | Taste | Sight | Smell | pH |
| Apple | 0.0 | Dark Brown Color with Mold | 0.0 | NC |
| Banana Juice | 0.0 | Dark Yellow Color with Mold | 0.0 | NC |

C. Quality Parameters of the Nanoemulsion with Encapsulated Natural Antioxidants 1. Encapsulation Efficiency This is measured as a percentage; it was performed through a relationship between the output and input of the efficient encapsulation process, taking an average of the tests performed with a standard deviation that shows the uncertainty of the repetitions in each run. An evaluation was considered of the best results obtained from the present invention, with respect to the best result stated in patent

| Comparative table-encapsulation efficiency (%) | |
|---|---|
| KR20160005182A | INVENTION |
| 77.87 ± 0.47 | 81.32 ± 0.16 |

The results show that patent KR20160005182A, at a concentration of 1.6% cinnamon oil, had an encapsulation efficiency of 77.87%, while with the patent filed, the antioxidant, at a concentration of 1.5%, had 81.32% efficiency.

2. Acute Toxicity

The ability of a substance to be lethal in low doses in humans (SINIA, 2017). The nanoemulsion mentioned in the invention was subjected to the oral LD50 ingestion toxicity test, according to the OECD Test Guideline 423, which consisted of a single dose to laboratory rats administering 2000 mg/kg of body weight, being observed for 14 days, a period of time that did not induce toxic damage and presented an LD50 higher than 2000 mg/kg of body weight, so the final product can be considered not classifiable as toxic or low intrinsic toxicity.

3. Nanoemulsion Particle Size Measurement

It was measured on a Mastersizer laser analyzer (<100 nm to >2 mm). The colloidal sample is placed on the optical bench of the measuring instrument, where a light beam illuminates the particles and the measurement is generated from different angles scattering the light throughout the sample. The invention presents an average particle size between 90-100 nm, at the 90th percentile.

4. Measurement of Zeta Potential (mV)

The measurement of the zeta potential of the nanoemulsion is a measurement of the electrical potential on the interfacial surface of suspensions; this is measured in electrophoretic cells with two electrodes connected to a source of energy (Kosegarten & Jimenez, 2012); it is associated with the pH value, as it associates the charge of the particles. A zeta-meter was used as a measurement instrument for the nanoemulsion in the invention; it yielded a value between −20 mV to −40 mV, depending on the concentrations of the inputs, and the pH was around 6.5 to 10, which shows adequate stability within the permitted range <−30 mV. Patent KR20160005182A, presents zeta potentials of about 0.5 to almost 6 mV, which could mean a high degree of dissociation.

5. Sanitary Microbiological Analysis

The sanitary microbiological analysis of the nanoemulsions applied to minimally processed foods was performed considering the growth of microorganisms such as mesophilic aerobics over time, under temperature conditions between 15-30° C. The colony count at 30° C. through the surface sowing technique resulted—at 14 days, in mangoes, avocados, mandarins (shelf at 30° C.); and 10 days in strawberries and camu-camu (shelf at 15° C.)—in favorable treatments that were in a ratio between 450-600 CFU/g of total aerobes. This indicator shows an improvement of between 200 and 250% for the same fruits compared to the blank which does not have any film.

6. Sensory Analysis

This is an experimental method that analyzes the organoleptic characteristics of a product, based on a panel of judges who perceive and qualify according to their criteria. The analysis of fresh mangoes filmed with the antioxidant-enriched nanoemulsion from mango waste was carried out in triplicate with a panel of 15 trained judges. The results of the above-mentioned test had an average score, from 1 to 5, of 5.0 points, which shows a slight improvement in the flavor of the product since the mango without application (control) obtained a score of 4.8 due to the enhancement of the fruity aroma. The results become more interesting when at 14 days the mango with the film obtains an average score of 3.9 points, while the control sample has a score of 0.0 due to its level of decomposition.

What is claimed is:

1. A process for producing a nanoemulsion formulation with encapsulated natural antioxidants for the preservation of fresh fruits, vegetables, cereals, juices and minimally processed foods, comprising the following stages:
   a. performing an extraction of natural antioxidants from peels or seeds of fruits, vegetables or cereals, wherein the extraction is carried out with pure water, with a concentration of natural antioxidants with a vacuum distillation method between 0.5-15 inches of Hg at 20-60° C. for 10-95 minutes until a concentration of natural antioxidants is between 10-50 wt. % and then a tangential nanofiltration is performed on the concentration of natural antioxidants;
   b. performing an encapsulation of the concentration of natural antioxidants generated after the tangential nanofiltration to produce encapsulated natural antioxidants;
   c. forming a nanoemulsion with the encapsulated natural antioxidants; and
   d. cryodrying the nanoemulsion with the encapsulated natural antioxidants.

2. The process for producing a nanoemulsion formulation with encapsulated natural antioxidants for the preservation of fresh fruits, vegetables, cereals, juices and minimally processed foods, according to claim 1, wherein the extraction of natural antioxidants comprises the following stages:
   a. sorting, washing and disinfecting the peels or seeds of the fruits, vegetables or cereals to produce disinfected peels or seeds;
   b. dehydration of the disinfected peels or seeds in a conventional oven at a temperature of 30-60° C. for 2-6 hours with air in reflux, or by freeze-drying at a temperature of −30-−50° C. and an absolute vacuum pressure of 0.04 mbar for 10-15 hours; up to a humidity of 2-40 wt. % to obtain dehydrated peels or seeds;
   c. extraction with pure water, from the dehydrated peels or seeds, assisted by microwaves at a power of 100-400 W for 5-40 minutes, or ultrasound with vibration power of 20-60 kHz, for 10-40 minutes at a temperature of 30-60° C., for obtaining extracted natural antioxidants;
   d. concentration of the extracted natural antioxidants with a vacuum distillation method in a rotovap under vacuum between 0.5-15 inches of Hg at 20-60° C. for 10-95 minutes until obtaining concentrated natural antioxidants between 10-50 wt. %; and,
   e. tangential nanofiltration of the concentrated natural antioxidants, with a pH of 6-10.5, in two sequential filters with 10-100 nm nanopores and a minimum surface area of 0.01 m², at a temperature of 30-60° C.; the concentrated natural antioxidants are pumped out at a pressure of 0.5-1 bar.

3. The process for producing a nanoemulsion formulation with encapsulated natural antioxidants for the preservation of fresh fruits, vegetables, cereals, juices and minimally processed foods, according to claim 1, wherein the encapsulation comprises the following stages:
   a. the concentration of natural antioxidants generated after the tangential nanofiltration mixed in a weight ratio of 1:1 with polysaccharides in an amount that replaces a percentage by weight of soluble solids measured with refractometry techniques to produce a mixture; the mixture is carried out at a speed of 500-2000 RPM, at a temperature between 20-60° C. for 1-3 hours;
b. homogenization at 8000-1500 RPM for 1-15 minutes, to produce the encapsulation, which is stored at a temperature of 5-15° C.

4. The process for producing a nanoemulsion formulation with encapsulated natural antioxidants for the preservation of fresh fruits, vegetables, cereals, juices and minimally processed foods, according to claim 1, wherein the nanoemulsion formulation with the encapsulated natural antioxidants comprises the following stages:
   a. dilution of alginic acid in drinking water, at a temperature of 50-70° C., with constant movement at 500-1500 RPM for 1-3 hours;
   b. homogenization at a speed of 8000-15000 RPM for about 1-15 minutes of the alginic acid in a solution with an oily matrix, polysorbate, glycerol and the encapsulated natural antioxidant;
   c. microfluidization at high pressures of 100-200 MPa, for 3-5 cycles.

5. The process for producing a nanoemulsion formulation with encapsulated natural antioxidants for the preservation of fresh fruits, vegetables, cereals, juices and minimally processed foods, according to claim 1, wherein the cryodrying of the nanoemulsion comprises nanoemulsion concentration through cryodrying methods.

6. The process for producing a nanoemulsion formulation with encapsulated natural antioxidants for the preservation of fresh fruits, vegetables, cereals, juices and minimally processed foods, according to claim 5, wherein the cryodrying is performed through freeze-drying, with a vacuum pressure of 0.04 mbar and a temperature of −10 to −15° C.

7. The process for producing a nanoemulsion formulation with encapsulated natural antioxidants for the preservation of fresh fruits, vegetables, cereals, juices and minimally processed foods according to claim 1, wherein the encapsulated natural antioxidants come from a combination of peels or seeds of fruits, vegetables or cereals, and the combination is a functional formula.

8. The process for producing a nanoemulsion formulation with encapsulated natural antioxidants for the preservation of fresh fruits, vegetables, cereals, juices and minimally processed foods according to claim 4, wherein the oily matrix is a combination of coconut, canola, almond, avocado or peanut oil.

9. The process for producing a nanoemulsion formulation with encapsulated natural antioxidants for the preservation of fresh fruits, vegetables, cereals, juices and minimally processed foods according to claim 4, wherein the formulation replaces glycerol and polysorbate for an amount of 1-5 wt % of calcium ascorbate or a 1:1 weight ratio combination of ascorbic acid and citric acid, and the food to be preserved is a fruit cut under refrigeration conditions.

10. The process for producing a nanoemulsion formulation with encapsulated natural antioxidants for the preservation of fresh fruits, vegetables, cereals, juices and minimally processed foods according to claim 1, wherein the process encapsulates proteins, vitamins and minerals, which have been extracted from fruits, vegetables or cereals.

* * * * *